(12) United States Patent
Nakane et al.

(10) Patent No.: US 7,138,261 B2
(45) Date of Patent: Nov. 21, 2006

(54) CELLULASE PREPARATIONS CONTAINING REDUCING AGENT AND METHOD OF PROCESSING FIBER

(75) Inventors: Akitaka Nakane, Saitama (JP); Jinichiro Koga, Saitama (JP); Hidetoshi Kubota, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 133 days.

(21) Appl. No.: 10/498,778

(22) PCT Filed: Dec. 17, 2002

(86) PCT No.: PCT/JP02/13173

§ 371 (c)(1),
(2), (4) Date: Jun. 15, 2004

(87) PCT Pub. No.: WO03/052105

PCT Pub. Date: Jun. 26, 2003

(65) Prior Publication Data

US 2005/0102762 A1    May 19, 2005

(30) Foreign Application Priority Data

Dec. 18, 2001  (JP) .............................. 2001-384037

(51) Int. Cl.
*C12N 9/24* (2006.01)
*C12Q 1/54* (2006.01)

(52) U.S. Cl. ................ 435/200; 435/252.3; 435/320.1; 435/14; 536/23.2

(58) Field of Classification Search ................ 435/200, 435/192, 252.3; 536/23.2, 23.7; 510/114, 510/392
See application file for complete search history.

(56) References Cited

U.S. PATENT DOCUMENTS

| 4,404,115 | A | | 9/1983 | Tai |
| 4,540,664 | A | | 9/1985 | Johnson et al. |
| 5,225,102 | A | | 7/1993 | Coyne et al. |
| 6,734,344 | B1 | * | 5/2004 | Laroche et al. ............. 800/288 |
| 6,921,655 | B1 | * | 7/2005 | Nakamura et al. .......... 435/200 |

FOREIGN PATENT DOCUMENTS

| EP | 0531372 | A1 | | 3/1993 |
| EP | 1123974 | A1 | | 8/2001 |
| JP | 10-001870 | | | 1/1998 |
| JP | 10042869 | | * | 2/1998 |

OTHER PUBLICATIONS

Luo et al. [Zhiwu Shengli Xuebao (2001). 27(6), 495-498].*
Mackenzie C.R. et al., Location and kinetic properties of the cellulose system of Acetivibrio cellulolyticus., Canadian Journal of Microbiology, 1982, vol. 28, No. 10, pp. 1158 to 1164; p. 1159 right column, line 34-47.
Sharma P. et al., Purification and properties of an endoglucanase from a Bacillus isolate., Enzyme Microbiol. technol. 1990. vol. 12, No. 2, pp. 132 to 137 p. 136, left column, lines 8 to 19.

* cited by examiner

*Primary Examiner*—Tekchand Saidha
(74) *Attorney, Agent, or Firm*—Sughrue Mion, PLLC

(57) ABSTRACT

A cellulase preparation comprising an endoglucanase derived from Zygomycetes, a cellulose-binding-domain-deleted endoglucanase, or a modified or homologous protein thereof, together with a reducing agent is disclosed. Further, a method of treating cellulose-containing fabric, comprising the step of treating the fabric with the cellulase preparation to improve a property of the fabric, a method of deinking waste paper, comprising the step of treating the waste paper with the cellulase preparation. together with a deinking agent, and a method of improving freeness of paper pulp, comprising the step of treating the paper pulp with the cellulase preparation, are disclosed.

15 Claims, No Drawings

CELLULASE PREPARATIONS CONTAINING REDUCING AGENT AND METHOD OF PROCESSING FIBER

TECHNICAL FIELD

The present invention relates to a cellulase preparation containing a reducing agent by which an endoglucanase activity is improved, and a method of treating a fabric using the cellulose preparation.

Background Art

Cellulase has three types of enzyme activities: a cellobiohydrolase activity which hydrolyzes solid crystal regions of cellulose from the nonreduced end in the exo manner to generate cellobiose; an endoglucanase activity which hydrolyzes amorphous regions of cellulose in the endo manner to transform cellulose molecules into low molecular weight molecules and to generate various types of cellooligosaccharides; and a β-glucosidase activity which decomposes cellobiose or cellooligosaccharides into glucose. Of these enzyme activities, it is known that cellulase having a high endoglucanase activity is advantageous when treating a fabric.

To impart desired properties to cellulose-containing fabric, the fabric has conventionally been treated with cellulase. For example, in the textile industry, treatment with cellulase is carried out to improve the touch and appearance of the cellulose-containing fabric, or to impart a "stonewash" appearance to the colored cellulose-containing fabric, thereby providing the fabric with localized color variations (EP Patent No. 307,564).

In such textile processing, cellulase derived from wood-rotting fungi such as *Trichoderma* or *Humicola* is mainly used. Such cellulase was used as a mixture comprising multiple cellulase components obtained by processing a culture filtrate of microorganisms having a cellulolytic activity. However, in order to achieve a greater economy, among cellulase preparations obtained by isolation from cellulase components, only endoglucanase, which mainly acts in fabric treatment, and which is genetically enhanced, has recently been used.

Examples of such an endoglucanase with a high activity include: EGV [Unexamined International Publication (Kohyo) No. 5-509223] and NCE4 (WO98/03640) derived from *Humicola insolens*, which strongly act on cotton fabrics; RCE I, RCE II, and RCE III derived from *Rhizopus oryzae*, which strongly act on lyocell fabrics; MCE I and MCE II derived from *Mucor circinelloides*; and PCE I derived from *Phycomyces nitens* (WO00/24879).

To improve the effects of the cellulase, the combined use of additives has also been attempted. For example, Unexamined International Publication (Kohyo) No. 5-507615 describes that a water-soluble polymer such as polyvinylpyrrolidone, polyvinyl alcohol, and polyacrylamide enhances the effects of *Humicola insolens*-derived cellulase and improves its activity of removing fuzz from colored fabrics. Further, it is known that a CMCase activity in the culture solution of *Trichoderma viride* is improved by the addition of Tween 20 (Ooshima, H. et al., Biotechnology and Bioengineering 28: 1727–1734, 1986). Furthermore, it is shown that the fuzz-removing activity of RCE I derived from *Rhizopus oryzae* is improved in the presence of a nonionic surfactant (WO02/38754).

DISCLOSURE OF THE INVENTION

The cellulases used for the above-described purposes are all expensive. Therefore, to achieve an industrial level application, the present inventors considered that a further improvement of the endoglucanase activity is desired, so that the above effects of cellulase can be more efficiently exerted. Further, where an attempt to obtain the effects of an improvement of the endoglucanase activity is carried out, the use of expensive additives increases costs in the textile processing treatment. Therefore, when selecting the additives, the present inventors considered that it is necessary to show the effects of the activity improvement by adding a low concentration of the additives, and that the additives should be readily available and inexpensive.

Therefore, the object of the present invention is to provide a cellulase preparation having the improved endoglucanase activity, which can be used in the fabric treatment for the purpose of improving cellulose-containing fabrics such that the removal of fuzz can be carried out efficiently and economically.

The present inventors have conducted intensive studies and, as a result, found that a reducing agent such as sodium thiosulfate or the like enhances the effects of Zygomycetes-derived endoglucanases such as RCE I, MCE I, PCE I, and the like at rates far higher than *Trichoderma*- and *Humicola*-derived known endoglucanases, and the present invention was completed.

The present invention relates to:

(1) a cellulase preparation comprising
an endoglucanase derived from Zygomycetes, a protein in which a cellulose binding domain is deleted in the endoglucanase, or a modified or homologous protein thereof; and
a reducing agent;

(2) the cellulase preparation described in (1), wherein the Zygomycetes is a microorganism belonging to genus *Rhizopus*, *Mucor*, or *Phycomyces*;

(3) a cellulase preparation comprising at least one of:
(a) a protein consisting of any one of the amino acid sequences of SEQ ID NOS: 1 to 6;
(b) a protein consisting of an amino acid sequence in which a cellulose binding domain is deleted in any one of the amino acid sequences of SEQ ID NOS: 1 to 6; or
(c) a protein consisting of an amino acid sequence in which one or plural amino acids are deleted, substituted, inserted, or added, in any one of the amino acid sequences of SEQ ID NOS: 1 to 6 or in an amino acid sequence in which a cellulose binding domain is deleted therein, and exhibiting an endoglucanase activity; and
a reducing agent;

(4) a cellulase preparation comprising a protein encoded by at least one of:
(a) a polynucleotide which encodes any one of the amino acid sequences of SEQ ID NOS: 1 to 6;
(b) a polynucleotide which encodes a protein consisting of an amino acid sequence in which a cellulose binding domain is deleted in any one of the amino acid sequences of SEQ ID NOS: 1 to 6; or
(c) a polynucleotide which encodes a protein exhibiting an endoglucanase activity and is complementary to a polynucleotide which hybridizes under stringent conditions to a polynucleotide which encodes a protein consisting of any one of the amino acid sequences of SEQ ID NOS: 1 to 6 or a protein consisting of an amino acid sequence in which a cellulose binding domain is deleted therein; and
a reducing agent;

(5) the cellulase preparation described in any one of (1) to (4), containing 0.01 to 50% by weight of the reducing agent in the cellulase preparation;
(6) the cellulase preparation described in any one of (1) to (5), in which the reducing agent is sodium thiosulfate, sodium sulfite, or thiourea;
(7) the cellulase preparation described in any one of (1) to (6), which is a granule not having a dustability or stabilized liquid;
(8) a method of treating cellulose-containing fabric, comprising the step of:

treating the fabric with the cellulase preparation described in any one of (1) to (7) to improve a property of the fabric;
(9) the method described in (8), wherein the improvement of the property of the fabric is a color clarification;
(10) the method described in (8), wherein the improvement of the property of the fabric is a removal of fuzz;
(11) the method described in (8), wherein the improvement of the property of the fabric is an addition of a stonewash-like appearance and texture;
(12) the method described in (8), wherein the improvement of the property of the fabric is an improvement of touch and appearance;
(13) the method described in (8), wherein the improvement of the property of the fabric is a softening of the fabric;
(14) the method described in any one of (8) to (13), wherein the treatment of the fabric with the cellulase preparation is carried out by soaking or rinsing the fabric;
(15) a method of deinking waste paper, comprising the step of:

treating the waste paper with the cellulase preparation described in any one of (1) to (7) together with a deinking agent; and
(16) a method of improving a freeness of paper pulp, comprising the step of:

treating the paper pulp with the cellulose preparation described in any one of (1) to (7).

BEST MODE FOR CARRYING OUT THE INVENTION

The present invention will be explained in detail hereinafter.

[1] Cellulase Preparation

The cellulase preparation of the present invention comprises one or more reducing agents and at least one of:
(1a) an endoglucanase derived from Zygomycetes;
(1b) a protein in which a cellulose binding domain is deleted in the Zygomycetes-derived endoglucanase (1a) [hereinafter sometimes referred to as "CBD-deleted endoglucanase"];
(1c) a modified protein of the Zygomycetes-derived endoglucanase (1a) or the CBD-deleted endoglucanase (1b) [hereinafter sometimes simply referred to as "modified protein"]; or
(1d) a homologous protein of the Zygomycetes-derived endoglucanase (1a) or the CBD-deleted endoglucanase (1b) [hereinafter sometimes simply referred to as "homologous protein"].

The term "endoglucanase" as used herein means endo-1,4-β-glucanase (EC 3.2.1.4), which has an activity of hydrolyzing the β-1,4-glucopyranosyl bond of β-1,4-glucan.

The term "endoglucanase activity" as used herein means a CMCase activity. The term "CMCase activity" as used herein means an activity of hydrolyzing carboxymethylcellulose (CMC; Tokyo Kasei Kogyo Co., Ltd.). When a solution containing a protein (enzyme) to be assayed and CMC is incubated for a predetermined period and the amount of reducing sugar released is measured, the amount of the enzyme producing the reducing sugar corresponding to 1 μmol of glucose per minute is defined as 1 unit of the CMCase activity.

The endoglucanase activity can be measured, for example, by the following procedure. That is, 0.5 mL of a solution containing a protein to be assayed is added to 0.5 mL of 2% CMC solution dissolved in 50 mmol/L acetate-sodium acetate buffer (pH 6.0), and the mixture is incubated at 50° C. for 30 minutes. A concentration of reducing sugar generated in the reaction mixture is measured by the 3,5-dinitrosalicylic acid method (DNS method). More particularly, after the incubation for 30 minutes, 3.0 mL of a DNS reagent is added to 1.0 mL of the reaction mixture, the whole is incubated in a boiling water bath for 5 minutes and diluted with 8.0 mL of distilled water, and the absorbance at 540 nm is measured. A calibration curve is drawn using glucose solutions prepared by stepwise dilution, and an amount of reducing sugar generated in the enzyme reaction mixture is determined as that of converted glucose. The activity is calculated by defining the amount of the enzyme producing the reducing sugar corresponding to 1 μmol of glucose per minute, as 1 unit.

The DNS reagent can be prepared in accordance with the disclosures in references such as Sakuzo Hukui, "Seikagaku Jikken-hou 1, Kangen-Tou no Teiryo-hou (Laboratory Manual for Biological Chemistry, Vol. 1, Assay of Reducing Sugar)", pp. 19–20, Japan Scientific Societies Press, or by the following procedure. To 300 mL of 4.5% aqueous solution of sodium hydrate, 880 mL of 1% 3,5-dinitrosalicylic acid solution and 255 g of Rochelle salt are added (Solution A). To 22 mL of 10% aqueous solution of sodium hydrate, 10 g of crystalline phenol is added, and then water is added so as to dissolve it and adjust the volume to 100 mL (Solution B). Then, 6.9 g of sodium hydrogencarbonate is dissolved in 69 mL of Solution B, and Solution A is poured thereinto. The whole is mixed with stirring so as to dissolve the Rochelle salt, allowed to stand for 2 days, and then filtrated.

As the endoglucanase derived from Zygomycetes which may be used in the present invention, there may be mentioned, for example, endoglucanases derived from *Rhizopus* sp., *Phycomyces* sp. or *Mucor* sp. More particularly, for example, RCE I (SEQ ID NO: 1), RCE II (SEQ ID NO: 2), RCE III (SEQ ID NO: 3), MCE I (SEQ ID NO: 4), MCE II (SEQ ID NO: 5), or PCE I (SEQ ID NO: 6) disclosed in WO00/24879 may be used. As the CBD-deleted endoglucanase, proteins in which the cellulose binding domain is deleted in the above-mentioned endoglucanases, such as CBD-deleted endoglucanases disclosed in WO02/42474, may be used. The CBD-deleted endoglucanases lack the cellulose binding domain, and exhibit the endoglucanase activity.

*Rhizopus oryzae* CP96001, from which the above-mentioned RCE I, RCE II, and RCE III are derived, was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Apr. 21, 1997, and was transferred to an international deposit on Sep. 24, 1999. The international deposit number (a number in parenthesis [ ] following the international deposit number is a domestic deposit number) is FERM BP-6889 [FERM P-16201].

*Mucor circinelloides* CP99001, from which the above-mentioned MCE I and MCE II are derived, was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Jul. 2, 1999, and was transferred to an international deposit on Sep. 24, 1999. The international deposit number (a number in parenthesis [ ] following the international deposit number is a domestic deposit number) is FERM BP-6890 [FERM P-17446].

*Phycomyces nitens* CP99002, from which the above-mentioned PCE I is derived, was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Jul. 2, 1999, and was transferred to an international deposit on Sep. 24, 1999. The international deposit number (a number in parenthesis [ ] following the international deposit number is a domestic deposit number) is FERM BP-6891[FERM P-17447].

The proteins which can be used in the cellulase preparation of the present invention include not only RCE I, RCE II, RCE III, MCE I, MCE II, and PCE I, and the CBD-deleted endoglucanases as described above, but also modified and/or homologous proteins thereof.

The term "modified protein" as used herein means a protein exhibiting the endoglucanase activity and consisting of an amino acid sequence in which one or plural (for example, one to several tens, more particularly, 1 to 50, preferably 1 to 30, more preferably 1 to 9) amino acids are deleted, substituted, inserted, or added in the amino acid sequence of RCE I, RCE II, RCE III, MCE I, MCE II, or PCE I, or any one of the CBD-deleted endoglucanases thereof.

The term "homologous protein" as used herein means a protein exhibiting the endoglucanase activity and having an amino acid sequence encoded by a polynucleotide (base sequence) complementary to a polynucleotide (base sequence) which hybridizes under stringent conditions to a polynucleotide (base sequence) which encodes the amino acid sequence of RCE I, RCE II, RCE III, MCE I, MCE II, or PCE I, or any one of the CBD-deleted endoglucanases thereof. The term "polynucleotide" as used herein includes DNA and RNA, and DNA is preferable.

The term "stringent conditions" as used herein means conditions in which a probe comprising a base sequence which encodes a partial or full-length sequence of
(a) the amino acid sequence of RCE I, RCE II, RCE III, MCE I, MCE II, or PCE I;
(b) the amino acid sequence of any one of the CBD-deleted endoglucanases thereof; or
(c) any one of the modified proteins thereof hybridizes to a polynucleotide which encodes a homologous protein, and the probe does not hybridize to the endoglucanase NCE 4 gene (SEQ ID NO: 7) described in WO98/03640 and the endoglucanase SCE 3 gene (SEQ ID NO: 8) described in WO98/54322. In this connection, it should be noted that the amount of each gene or polynucleotide used herein is equivalent to the amount of each of the NCE 4 gene, the SCE 3 gene, and the polynucleotide encoding a homologous protein.

More particularly, it means conditions in which, for example, using as a probe a labeled full-length DNA sequence encoding the amino acid sequence of RCE I, pre-hybridization is carried out at 42° C. for 1 hour according to the protocol attached to the ECL direct DNA/RNA labeling and detection system (Amersham), then the above probe is added thereto followed by hybridization at 42° C. for 15 hours, and thereafter, the resultant product is washed twice with 0.5×SSC (1×SSC; 15 mmol/L trisodium citrate, 150 mmol/L sodium chloride) containing 0.4% SDS and 6 mol/L urea at 42° C. for 20 minutes, and finally followed by washing the product twice with 5×SSC at room temperature for 10 minutes.

The above-mentioned "polynucleotide (base sequence) which encodes the amino acid sequence of RCE I, RCE II, RCE III, MCE I, MCE II, or PCE I" includes a polynucleotide in which codon usage and/or an intron recognition sequence are optimized in accordance with the type of a host cell used for transformation, such as the codon-optimized endoglucanase RCE I gene (SEQ ID NO: 9) described in WO00/24879.

As the modified or homologous protein, there may be mentioned, for example, a protein having an amino acid sequence having preferably an 80% or more homology, more preferably a 90% or more homology, still further preferably a 95% or more homology, most preferably a 98% or more homology, with that of RCE I, RCE II, RCE III, MCE I, MCE II, or PCE I, or any one of the CBD-deleted endoglucanases thereof. In this connection, the above values of homology may be values calculated using a known program for homology search, preferably values calculated using FASTA3 (Science, 227, 1435–1441 (1985); Proc. Natl. Acad. Sci. USA, 85, 2444–2448 (1988); see also the DNA Databank of Japan website having the world wide web (www.) suffix ddbj.nig.ac.jp/E-mail/homology-j.html) in accordance with default parameters.

The "reducing agent", which is contained in the cellulase preparation of the present invention, means a substance having an activity of reducing a molecule by accepting electrons from the molecule, thereby being itself oxidized. It is known that such reducing agents exhibit an activity of reducing and removing the remaining chlorine or the like in tap water. As the reducing agent used in the present invention, an inorganic reducing agent is preferable, and a substance which inhibits the enzyme activity cannot be used. Examples thereof include sulfurous acid, disulfurous acid, and thiosulfuric acid, and salts thereof, and thiourea. The reducing agents can be used alone or in a combination thereof.

The cellulose preparation of the present invention may comprise components which are conventionally contained in cellulase preparations such as excipients and/or preservatives. The form of the cellulose preparation may be solid or liquid. Examples of the form include powder, particulate, granule, non-dusting granule and liquid formulation.

The non-dusting granule (preferably a granule not having a dustability) that is one form of cellulase preparation can be produced according to the common dry granulation method. That is to say, powder cellulase enzyme is mixed with one or plural substances selected from the group comprising inorganic salts such as sodium sulfate or sodium chloride which are neutral and do not have an effect on the endoglucanase activity; minerals such as bentonite or montmorillonite which do not have an effect on the endoglucanase activity; neutral organic substances such as starch or powder cellulose; and surfactants. Thereafter, the powders or the finely suspended suspension of one or plural reducing agents which improve the effects of endoglucanase are added to the mixture, and then the obtained product is fully mixed or kneaded.

Depending on the situation, a synthetic polymer such as polyethylene glycol or a natural polymer such as starch, which binds solids, is optionally added to the mixture and further kneaded. Thereafter, granulation is carried out by extrusion molding, using, for example, a disk pelleter, and the obtained molded material is then converted into a spherical form using a marumerizer followed by drying, so that non-dusting granules can be produced. Naturally, it is also possible to coat the surface of granules with a polymer or the like to control the permeation of oxygen or water. In this case, one or plural reducing agents which improve the effect of endoglucanase can be added to the cellulase preparation at a ratio of 0.01 to 50% by weight, preferably 0.1 to 20% by weight, more preferably 0.1 to 10% by weight.

Further, the liquid preparation (preferably stabilized liquid) can be prepared by blending an endoglucanase stabilizer such as a synthetic or natural polymer with a cellulase enzyme solution and, if necessary, adding inorganic salts and/or a synthetic preservative. In this case, one or plural reducing agents which improve the effect of endoglucanase can be added. Similar to the case of the non-dusting granule, one or plural reducing agents which improve the effect of endoglucanase can be added to the cellulase preparation at a ratio of 0.01 to 50% by weight, preferably 0.1 to 20% by weight, more preferably 0.1 to 10% by weight.

[2] Method of Treating Fabric

The method of treating fabric according to the present invention comprising the step of:

treating cellulose-containing fabric with the above-mentioned cellulase preparation.

The following properties of cellulose-containing fabric can be improved by the present treatment method:
(1) Color clarification of colored cellulose-containing fabric;
(2) Removal of fuzz (reduction of the rate of the formation of fuzz, and reduction of fuzz);
(3) Providing of localized color variation to colored cellulose-containing fabric, that is, providing a stonewash-like appearance and texture to colored cellulose-containing fabric, typically jeans;
(4) Improvement of the touch and appearance of fabric by reducing weight; and
(5) Softening of fabric (reduction of stiffness).

More particularly, the method of treating fabric according to the present invention can be carried out by adding the cellulase preparation of the present invention into water in which fabric is or will be soaked, for example, during a soaking or rinsing of fabric.

Conditions such as contact temperature or the amount of endoglucanase may be appropriately determined in accordance with various other conditions. For example, when reducing the rate of the formation of fuzz or reducing fuzz of the cellulose-containing fabric, the fabric can be treated at a temperature of approximately 30 to 60° C., using 0.2 µg/mL or more of reducing agents and endoglucanases in a protein concentration of 0.001 to 20 mg/L. One or more reducing agents may be added, taking into consideration economical effects, so long as an amount thereof is 0.2 µg/mL or more and the reducing agent does not inhibit the enzyme activity. Preferably 0.2 to 500 µg/mL, more preferably 0.3 to 150 µg/mL thereof may be used.

When providing a localized color variation to colored cellulose-containing fabric, the fabric can be treated at a temperature of approximately 40 to 60° C., using 0.2 µg/mL or more of reducing agents and endoglucanases in a protein concentration of 0.01 to 100 mg/L. One or more reducing agents may be added, taking into consideration economical effects, so long as an amount thereof is 0.2 µg/mL or more and the reducing agent does not inhibit the enzyme activity. Preferably 0.2 to 500 µg/mL, more preferably 0.3 to 150 µg/mL thereof may be used.

In a processing of reducing weight to improve the touch and appearance of the cellulose-containing fabric, the fabric can be treated at a temperature of approximately 30 to 60° C., using 0.2 µg/mL or more of reducing agents and endoglucanases in a protein concentration of 0.001 to 100 mg/L. One or more reducing agents may be added, taking into consideration economical effects, so long as an amount thereof is 0.2 µg/mL or more and the reducing agent does not inhibit the enzyme activity. Preferably 0.2 to 500 µg/mL, more preferably 0.3 to 150 µg/mL thereof may be used.

The protein concentration of each type of endoglucanase can be calculated, for example, by HPLC analysis using TSKgel TMS-250 column (4.6 mm I.D. ×7.5 cm) (TOSOH Corporation). The HPLC analysis involves loading acetonitrile in 0.05% TFA (trifluoroacetic acid) with a linear concentration gradient of 0% to 80% at a flow rate of 1.0 mL/min so as to elute each type of endoglucanase, and calculating the protein concentration from the peak area at UV 280 nm. For example, a purified NCE4, the protein concentration of which is previously determined by a Protein Assay Kit (BioRad Laboratories), is subjected to the HPLC analysis in the same manner as above, so that it can be used as a standard. The purified NCE4 can be obtained, for example, by cultivating *Humicola insolens* MN200-1 and purifying it from the culture, in accordance with the method described in WO98/03640. As a standard for the determination of a protein concentration in the Protein Assay Kit, for example, Albumin Standard (Bovin serum albumin, fraction V; PIERCE) can be used.

[3] Method of Deinking Waste Paper

The method of deinking waste paper according to the present invention comprises the step of:

treating the waste paper with the above-mentioned cellulase preparation together with a deinking agent.

More particularly, the present method can be carried out by treating waste paper with the cellulase preparation of the present invention together with a deinking agent, in a deinking step in a process of producing recycled paper from waste paper. The present method enables the deinking of waste paper, and thus the whiteness of waste paper can be improved. Waste paper which can be treated by the present method includes all types of common waste paper, for example, used newspaper, used magazine paper, and low to middle grade printed used paper which comprise mechanical pulp and chemical pulp; used wood-free paper comprising chemical pulp; and printed waste paper thereof such as coating paper. The deinking agent means an agent commonly used in the deinking of waste paper. Examples of the deinking agent include sodium chloride, alkalis such as sodium carbonate, sodium silicate, hydrogen peroxide, phosphates, anionic or nonionic surfactants, scavengers such as oleic acid, and assistant agents such as a pH stabilizer, a chelating agent, or a dispersing agent.

[4] Method of Improving Freeness of Paper Pulp

The method of improving the freeness of paper pulp according to the present invention comprises the step of:

treating the paper pulp with the above-mentioned cellulase preparation.

More particularly, the present method can be carried out by treating paper pulp with the cellulase preparation of the present invention. Examples of paper pulp which can be treated by the present method include waste paper pulp, recycled paperboard pulp, kraft pulp, sulfite pulp, thermomechanical treatment pulp, and other high-yield pulp.

EXAMPLES

The present invention now will be further illustrated by, but is by no means limited to, the following Examples.

All publications and patent applications mentioned in the present specification are herein incorporated by reference.

Example 1

Comparison Among Improvement Ratios of Fuzz-Removing Activities of Various Types of Cellulases by Addition of Reducing Agent The cultivation of *Rhizopus oryzae*, *Mucor circinelloides*, and *Phycomyces nitens*, and the purification of RCE I, MCE I, and PCE I endoglucanases from the cultures were carried out by the method described in WO00/24879.

The cultivation of *Humicola insolens* MN200-1 and the purification of NCE4 endoglucanase from the culture were carried out by the method described in WO98/03640. The strain was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Jul. 15, 1996, and was transferred to an international deposit on Jun. 13, 1997. The international deposit number (a number in parenthesis [ ] following the international deposit number is a domestic deposit number) is FERM BP-5977 [FERM P-15736].

The cultivation of *Trichoderma viride* MC300-1 was carried out by the method described in WO98/54332. The strain was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Sep. 9, 1996, and was transferred to an international deposit on Aug. 11, 1997. The international deposit number (a number in parenthesis [ ] following the international deposit number is a domestic deposit number) is FERM BP-6047 [FERM P-15842].

Fuzz-removing treatment of a cotton knit fabric with fuzz formed in a large washer (a fabric of 6 cm×8 cm from Cotton Smooth Knit No. 3900, Nitto Boseki Co., Ltd. dyed brown by reactive dyeing in Tsuyatomo-Senko) was carried out using each of the obtained culture supernatants under the following conditions:

(Test Conditions)

Testing machine: Launder Meter L-20 (Daiei Kagaku Seiki MFG., Japan)
Temperature: 58° C. (only the *Trichoderma viride* culture supernatant); 40° C. (all other enzyme solutions)
Time: 120 minutes
Amount of reaction solution: 100 mL
Reaction pH: pH 4.5 (5 mmol/L acetate buffer) (only the *Trichoderma viride* culture supernatant pH 7.0 (5 mmol/L phosphate buffer) (all other enzyme solutions). All the buffers were prepared using tap water.
Type and amount of reducing agent: 1.2 µg/mL sodium thiosulfate pentahydrate (Wako Pure Chemical Industries, Co., Ltd.)

To each of the treating solutions, four of about 16 g rubber balls were added together with each enzyme solution.

The amount of the enzyme solution required to remove approximately 50% of the formed fuzz on the basis of visual evaluation was determined in each of both cases of adding and not adding the reducing agent. Thereafter, a value was obtained by dividing the amount of the enzyme solution required to remove approximately 50% of the fuzz when not adding the reducing agent by the amount when adding the reducing agent, and the obtained value was defined as an improvement ratio of the fuzz-removing activity by the addition of the reducing agent. The results are shown in Table 1.

TABLE 1

| Enzyme solutions | Improvement ratio of fuzz-removing activity by addition of reducing agent (fold) |
|---|---|
| *Humicola insolens* culture supernatant | 1.2 |
| *Trichoderma viride* culture supernatant | 1.1 |
| Purified NCE4 | 1.2 |
| Purified RCEI | 5.0 |
| Purified MCEI | 3.5 |
| Purified PCEI | 2.5 |

From the results of Table 1, it is found that the fuzz-removing activity of RCE I, MCE I, and PCE I, which are endoglucanases derived from Zygomycetes, is improved by the addition of the reducing agent at a level far higher than culture supernatants (i.e., cellulase) derived from *Humicola insolens* and *Trichoderma viride*.

Example 2

Improvement Effect of Fuzz-Removing Activity of RCE I Expressed in *Humicola* by Addition of Various Reducing Agents RCE I endoglucanase was expressed in *Humicola insolens* in accordance with the method described in Examples D3 and D4 of WO00/24879. Fuzz-removing treatment of a cotton knit fabric with fuzz formed in a large washer (a fabric of 6 cm×8 cm from Cotton Smooth Knit No. 3900, Nitto Boseki Co., Ltd. dyed brown by reactive dyeing in Tsuyatomo-Senko) was carried out using the obtained culture supernatant under the following conditions:

(Test Conditions)

| | |
|---|---|
| Testing machine: | Launder Meter L-20 (Daiei Kagaku Seiki MFG., Japan) |
| Temperature: | 40° C. |
| Time: | 120 minutes |
| Amount of reaction solution: | 100 mL |
| Reaction pH: | pH 7.0 (5 mmol/L phosphate buffer; prepared using tap water) |
| Amount of reducing agent: | 1.2 µg/mL |
| Type of reducing agent: | sodium thiosulfate pentahydrate (Wako Pure Chemical Industries, Co., Ltd.); sodium sulfite (anhydride) (Wako Pure Chemical Industries, Co., Ltd.); and thiourea (Kanto Kagaku, Co., Ltd.). |

To each of the treating solutions, four of about 16 g rubber balls were added together with the enzyme solution.

The amount of the enzyme solution required to remove approximately 50% of the formed fuzz on the basis of visual evaluation was determined in each of both cases of adding and not adding the various reducing agents. Thereafter, a value was obtained by dividing the amount of the enzyme solution required to remove approximately 50% of the fuzz when not adding the reducing agent by the amount when adding each of the various reducing agents, and the obtained value was defined as an improvement ratio of the fuzz-removing activity by the addition of each of the various reducing agents. The results are shown in Table 2.

TABLE 2

| Reducing agents | Improvement ratio of fuzz-removing activity by addition of reducing agent (fold) |
|---|---|
| Sodium thiosulfate pentahydrate | 5.0 |
| Sodium sulfite (anhydride) | 5.0 |
| Thiourea | 5.0 |

From the results of Table 2, it is found that the fuzz-removing activity of the culture supernatant obtained by expressing and secreting RCE I in *Humicola insolens* was improved by any of the above reducing agents.

Example 3

Improvement Effect of Fuzz-Removing Activity of RCE I Expressed in *Humicola* by addition of Reducing Agent with Various Concentrations RCE I endoglucanase was expressed in *Humicola insolens* in accordance with the method described in Examples D3 and D4 of WO00/24879. Fuzz-removing treatment of a cotton knit fabric with fuzz formed in a large washer (a fabric of 6 cm×8 cm from Cotton Smooth Knit No. 3900, Nitto Boseki Co., Ltd. dyed brown by reactive dyeing in Tsuyatomo-Senko) was carried out using the obtained culture supernatant under the following conditions:

(Test Conditions)

| | |
|---|---|
| Testing machine: | Launder Meter L-20 (Daiei Kagaku Seiki MFG., Japan) |
| Temperature: | 40° C. |
| Time: | 120 minutes |
| Amount of reaction solution: | 100 mL |
| Reaction pH: | pH 7.0 (5 mmol/L phosphate buffer; prepared using tap water) |
| Type of reducing agent: | sodium thiosulfate pentahydrate (Wako Pure Chemical Industries, Co., Ltd.) Amount of reducing agent: 0.15 to 150 μg/mL |

To each of the treating solutions, four of about 16 g rubber balls were added together with the enzyme solution.

The amount of the enzyme solution required to remove approximately 50% of the formed fuzz on the basis of visual evaluation was determined in each of cases of adding various concentrations of the reducing agent. Thereafter, a value was obtained by dividing the amount of the enzyme solution required to remove approximately 50% of the fuzz when not adding the reducing agent by the amount when adding each of various concentrations of the reducing agent, and the obtained value was defined as an improvement ratio of the fuzz-removing activity by the addition of each of various concentrations of the reducing agent. The results are shown in Table 3.

TABLE 3

| Amount of reducing agent (μg/ml) | Improvement ratio of fuzz-removing activity by addition of reducing agent (fold) |
|---|---|
| 0.15 | 1.0 |
| 0.3 | 2.5 |
| 0.6 | 4.5 |
| 0.9 | 5.0 |
| 1.2 | 5.0 |
| 1.8 | 4.5 |
| 3.0 | 4.5 |
| 6.0 | 4.5 |
| 15.0 | 4.5 |
| 30.0 | 4.5 |
| 60.0 | 4.0 |
| 150.0 | 4.0 |

From the results of Table 3, it is found that the fuzz-removing activity of the culture supernatant obtained by expressing and secreting RCE I in *Humicola insolens* was improved by the addition of the reducing agent having a wide range of concentration from 0.3 μg/mL to 150 μg/mL or more.

Example 4

Production of RCE I Cellulase Preparation Comprising Reducing Agent

After mixing the following raw materials by the mixing ratios as described in Table 4, an appropriate amount of water was added thereto, and the mixture was kneaded. The obtained product was subjected to a disk pelleter for molding, and the product obtained by injection molding was converted in a particle form using a marumerizer (Fuji Paudal Co., Ltd.) followed by drying and sieving the product so as to obtain a granulated product.

TABLE 4

| Raw materials | Mixing ratio (%) |
|---|---|
| Sodium thiosulfate | 1 |
| S-220 (nonionic surfactant manufactured by NOF Corporation) | 10 |
| RCE I cellulase powder product | 5 |
| Magnesium chloride | 0.5 |
| Monopotassium phosphate (Wako Pure Chemical Industries, Co., Ltd.) | 2 |
| Dipotassium phosphate (Wako Pure Chemical Industries, Co., Ltd.) | 1 |
| Corn starch (Shikishima Starch Co.) | 80.5 |

The RCE I cellulase powder product was prepared by concentrating the culture supernatant of RCE I expressed in *Humicola insolens* using ultrafiltration, according to the method described in Examples D3 and D4 of WO00/24879, followed by spray drying.

INDUSTRIAL APPLICABILITY

The present invention provides a cellulase preparation having a dramatically improved Zygomycetes-derived endoglucanase activity by adding a reducing agent into the preparation. When the cellulase preparation is used in the treatment of fabric (such as the reduction of fuzz of cellulose-containing fabric, the improvement of touch and appearance, the color clarification, localized color variation, or softening), the deinking of waste paper, or the processing of improving the freeness of paper pulp, each of the above treatments can be carried out with a less amount of enzyme, thereby significantly reducing cost.

Free Text in Sequence Listing

Features of "Artificial Sequence" are described in the numeric identifier <223> in the Sequence Listing. More particularly, the base sequence of SEQ ID NO: 9 is a codon-optimized sequence corresponding to RCE I protein (SEQ ID NO: 1).

Although the present invention has been described with reference to specific embodiments, various changes and modifications obvious to those skilled in the art are possible without departing from the scope of the appended claims.

The invention claimed is:

1. A composition comprising an endoglucanase and a reducing agent, wherein said endoglucanase is selected from the group consisting of:
    (a) the polypeptide set forth in SEQ ID NO:1.
    (b) the polypeptide set forth in SEQ ID NO:1 lacking a cellulose binding domain,
    (c) a polypeptide having 90% or more homology with the polypeptide of (a),
    (d) a polypeptide having 90% or more homology with the polypeptide of (b), and
    (e) a polypeptide encoded by a polynucleotide the complement of which hybridizes under stringent hybridization conditions to a polynucleotide encoding the polypeptide of SEQ ID NO:1, wherein said stringent hybridization conditions comprise hybridization at 42° C. for 15 hours, two washes with 0.5 ×SSC containing 0.4% SDS and 6 mol/L urea at 42° C. for 20 minutes, and one wash with 5 ×SSC at room temperature for 10 minutes, wherein said polypeptides (c), (d) and (e) have endoglucanase activity.

2. The composition according to claim 1, wherein said reducing agent is present in an amount of 0.01 to 50% by weight.

3. The composition according to claim 1, wherein said reducing agent is selected from the group consisting of sodium thiosulfate, sodium sulfite, and thiourea.

4. The composition according to claim 1, wherein said composition is in the form of a granule or a stabilized liquid, wherein said granule does not have a dustability.

5. A method of improving a property of a cellulose-containing fabric, comprising treating a cellulose-containing fabric with a composition according to claim 1, thereby improving property of a cellulose-containing fabric.

6. The method according to claim 5, wherein said improved property is a color clarification of said fabric.

7. The method according to claim 5, wherein said improved property is a removal of fuzz from said fabric.

8. The method according to claim 5, wherein said improved property is an addition of a stonewash-like appearance and texture to said fabric.

9. The method according to claim 5, wherein said improved property is an improvement of touch and appearance of said fabric.

10. The method according to claim 5, wherein said improved property is a softening of said fabric.

11. The method according to claim 5, wherein said treating is soaking or rinsing said fabric in a composition of claim 1.

12. A method of deinking waste paper, comprising treating waste paper with a composition of claim 1 in the presence of a deinking agent, thereby deinking waste paper.

13. A method of improving a freeness of paper pulp, comprising treating paper pulp with a composition of claim 1, thereby improving a freeness of paper pulp.

14. The composition according to claim 1, wherein said endoglucanase is the polypeptide set forth in SEQ ID NO:1.

15. The composition according to claim 1, wherein said endoglucanase is the polypeptide set forth in SEQ ID NO:1 lacking a cellulose binding domain.

* * * * *

SEQUENCE LISTING

```
<160> NUMBER OF SEQ ID NOS: 9

<210> SEQ ID NO 1
<211> LENGTH: 338
<212> TYPE: PRT
<213> ORGANISM: Rhizopus oryzae CP96001
<220> FEATURE:
<221> NAME/KEY: sig_peptide
<222> LOCATION: (-23)..(-1)
<220> FEATURE:
<221> NAME/KEY: mat_peptide
<222> LOCATION: (1)..(315)

<400> SEQUENCE: 1

Met Lys Phe Ile Thr Ile Ala Ser Ser Ala Leu Leu Ala Leu Ala Leu
            -20                 -15                 -10

Gly Thr Glu Met Ala Ser Ala Ala Glu Cys Ser Lys Leu Tyr Gly Gln
         -5                   1               5

Cys Gly Gly Lys Asn Trp Asn Gly Pro Thr Cys Cys Glu Ser Gly Ser
 10                  15                  20                  25

Thr Cys Lys Val Ser Asn Asp Tyr Tyr Ser Gln Cys Leu Pro Ser Gly
                 30                  35                  40

Ser Ser Gly Asn Lys Ser Ser Glu Ser Ala His Lys Lys Thr Thr Thr
                 45                  50                  55

Ala Ala His Lys Lys Thr Thr Thr Ala Ala His Lys Lys Thr Thr Thr
             60                  65                  70

Ala Pro Ala Lys Lys Thr Thr Thr Val Ala Lys Ala Ser Thr Pro Ser
 75                  80                  85

Asn Ser Ser Ser Ser Ser Gly Lys Tyr Ser Ala Val Ser Gly Gly
 90                  95                 100                 105

Ala Ser Gly Asn Gly Val Thr Thr Arg Tyr Trp Asp Cys Cys Lys Ala
                110                 115                 120

Ser Cys Ser Trp Pro Gly Lys Ala Asn Val Ser Ser Pro Val Lys Ser
             125                 130                 135

Cys Asn Lys Asp Gly Val Thr Ala Leu Ser Asp Ser Asn Ala Gln Ser
             140                 145                 150

Gly Cys Asn Gly Gly Asn Ser Tyr Met Cys Asn Asp Asn Gln Pro Trp
 155                 160                 165

Ala Val Asn Asp Asn Leu Ala Tyr Gly Phe Ala Ala Ala Ile Ser
 170                 175                 180                 185

Gly Gly Gly Glu Ser Arg Trp Cys Cys Ser Cys Phe Glu Leu Thr Phe
             190                 195                 200

Thr Ser Thr Ser Val Ala Gly Lys Lys Met Val Val Gln Val Thr Asn
             205                 210                 215

Thr Gly Gly Asp Leu Gly Ser Ser Thr Gly Ala His Phe Asp Leu Gln
         220                 225                 230

Met Pro Gly Gly Val Gly Ile Phe Asn Gly Cys Ser Ser Gln Trp
 235                 240                 245
```

```
Gly Ala Pro Asn Asp Gly Trp Gly Ser Arg Tyr Gly Ile Ser Ser
250                 255                 260                 265

Ala Ser Asp Cys Ser Ser Leu Pro Ser Ala Leu Gln Ala Gly Cys Lys
            270                 275                 280

Trp Arg Phe Asn Trp Phe Lys Asn Ala Asp Asn Pro Ser Met Thr Tyr
            285                 290                 295

Lys Glu Val Thr Cys Pro Lys Glu Ile Thr Ala Lys Thr Gly Cys Ser
            300                 305                 310

Arg Lys

<210> SEQ ID NO 2
<211> LENGTH: 366
<212> TYPE: PRT
<213> ORGANISM: Rhizopus oryzae CP96001
<220> FEATURE:
<221> NAME/KEY: sig_peptide
<222> LOCATION: (-23)..(-1)
<220> FEATURE:
<221> NAME/KEY: mat_peptide
<222> LOCATION: (1)..(343)

<400> SEQUENCE: 2

Met Lys Phe Ile Thr Ile Thr Ser Ser Ala Leu Leu Ala Leu Ala Leu
            -20                 -15                 -10

Gly Thr Glu Met Ala Ser Ala Ala Lys Cys Ser Lys Leu Tyr Gly Gln
        -5                   1                   5

Cys Gly Gly Lys Asp Trp Asn Gly Pro Thr Cys Cys Glu Ser Gly Ser
 10                  15                  20                  25

Thr Cys Lys Val Ser Asn Asp Tyr Tyr Ser Gln Cys Leu Ala Pro Glu
             30                  35                  40

Ser Asn Gly Asn Lys Ser Ser Glu Cys Ser Lys Leu Tyr Gly Gln Cys
             45                  50                  55

Gly Gly Lys Asp Trp Asn Gly Pro Thr Cys Cys Glu Ser Gly Ser Thr
         60                  65                  70

Cys Lys Val Ser Asn Asp Tyr Tyr Ser Gln Cys Leu Ala Pro Glu Ser
 75                  80                  85

Asn Gly Asn Lys Thr Ser Glu Ser Ala His Lys Thr Thr Thr Thr Thr
 90                  95                 100                 105

Ala Pro Ala Lys Glu Ile Thr Thr Thr Ala Lys Ala Ser Asn Ser Ser
            110                 115                 120

Asn Ser Ser Gly Lys Tyr Ser Ile Val Ser Gly Gly Ala Ser Gly Asn
            125                 130                 135

Gly Val Thr Thr Arg Tyr Trp Asp Cys Cys Lys Ala Ser Cys Ser Trp
        140                 145                 150

Pro Gly Lys Ala Asn Val Ser Ser Pro Val Lys Ser Cys Asn Lys Asp
    155                 160                 165

Gly Val Thr Ala Leu Ser Asp Ser Asn Val Gln Ser Gly Cys Asn Gly
170                 175                 180                 185

Gly Asn Ser Tyr Met Cys Asn Asp Asn Gln Pro Trp Ala Val Asn Asp
            190                 195                 200

Asn Leu Ala Tyr Gly Phe Ala Ala Ala Ile Ser Gly Gly Gly Gly Glu
            205                 210                 215

Ser Arg Trp Cys Cys Ser Cys Phe Glu Leu Thr Phe Thr Ser Thr Ser
            220                 225                 230

Val Ala Gly Lys Lys Met Val Ile Gln Val Thr Asn Thr Gly Gly Asp
            235                 240                 245
```

```
Leu Gly Ser Ser Thr Gly Ala His Phe Asp Leu Gln Met Pro Gly Gly
250                 255                 260                 265

Gly Val Gly Ile Phe Asn Gly Cys Ser Lys Gln Trp Gly Ala Pro Asn
                270                 275                 280

Asp Gly Trp Gly Ser Arg Tyr Gly Gly Ile Ser Ser Ala Ser Asp Cys
            285                 290                 295

Ser Ser Leu Pro Ser Ala Leu Gln Ala Gly Cys Lys Trp Arg Phe Asn
        300                 305                 310

Trp Phe Lys Asn Ala Asp Asn Pro Ser Met Thr Tyr Lys Glu Val Thr
    315                 320                 325

Cys Pro Lys Glu Ile Thr Ala Lys Thr Gly Cys Ser Arg Lys
330                 335                 340
```

<210> SEQ ID NO 3
<211> LENGTH: 360
<212> TYPE: PRT
<213> ORGANISM: Rhizopus oryzae CP96001
<220> FEATURE:
<221> NAME/KEY: sig_peptide
<222> LOCATION: (-23)..(-1)
<220> FEATURE:
<221> NAME/KEY: mat_peptide
<222> LOCATION: (1)..(337)

<400> SEQUENCE: 3

```
Met Lys Phe Leu Thr Ile Ala Ser Ser Ala Ile Leu Ala Leu Ala Val
            -20                 -15                 -10

Gly Thr Glu Met Ala His Ala Ala Glu Cys Ser Lys Ala Tyr Tyr Gln
        -5                   1                   5

Cys Gly Gly Lys Asn Trp Asp Gly Pro Thr Cys Cys Glu Ser Gly Ser
10                  15                  20                  25

Thr Cys Val Asp Tyr Pro Asp Asn Pro Phe Tyr Ser Gln Cys Val Pro
                30                  35                  40

Asn Glu Asn Leu Thr Ser Thr Asn Lys Ser Ser His Lys Thr Thr Thr
            45                  50                  55

Thr Glu Ser Ala Lys Lys Thr Thr Thr Lys Gly Ser Lys Lys Thr
        60                  65                  70

Thr Thr Thr Glu Ala Ser Lys Lys Thr Thr Thr Glu Ala Ser Lys
    75                  80                  85

Lys Thr Thr Thr Thr Glu Ala Ser Lys Lys Thr Thr Thr Thr Lys
90                  95                  100                 105

Lys Ala Ser Thr Ser Thr Ser Ser Ser Ser Ala Ser Thr Asn
                110                 115                 120

Tyr Ser Ala Val Ser Gly Gly Ala Ser Gly Asn Gly Glu Thr Thr Arg
            125                 130                 135

Tyr Trp Asp Cys Cys Lys Pro Ser Cys Ser Trp Pro Gly Lys Ala Asp
        140                 145                 150

Val Thr Ser Pro Val Gly Ser Cys Asn Lys Asp Gly Lys Thr Leu Ala
    155                 160                 165

Asp Asn Asn Thr Gln Asn Gly Cys Val Gly Gly Ser Ser Tyr Thr Cys
170                 175                 180                 185

Asn Asp Asn Gln Pro Trp Val Val Ser Asp Asp Leu Ala Tyr Gly Phe
                190                 195                 200

Ala Ala Ala Ser Ile Ser Gly Ser Glu Ala Thr Trp Cys Cys Ala
            205                 210                 215

Cys Phe Glu Leu Thr Phe Thr Ser Thr Ala Val Lys Gly Lys Lys Met
        220                 225                 230
```

```
Val Val Gln Val Thr Asn Thr Gly Ser Asp Leu Gly Ser Asn Thr Gly
    235                 240                 245

Ala His Phe Asp Leu Gln Met Pro Gly Gly Gly Val Gly Ile Tyr Asn
250                 255                 260                 265

Gly Cys Ala Thr Gln Trp Gly Ala Pro Thr Asp Gly Trp Gly Ala Arg
                270                 275                 280

Tyr Gly Gly Val Ser Ser Ala Ser Asp Cys Ser Asn Leu Pro Ser Ala
            285                 290                 295

Leu Gln Ala Gly Cys Lys Trp Arg Phe Gly Trp Phe Lys Asn Ala Asp
        300                 305                 310

Asn Pro Thr Met Thr Tyr Lys Gln Val Thr Cys Pro Lys Ala Ile Thr
    315                 320                 325

Ala Lys Ser Gly Cys Ser Arg Lys
330                 335

<210> SEQ ID NO 4
<211> LENGTH: 338
<212> TYPE: PRT
<213> ORGANISM: Mucor circinelloides CP99001
<220> FEATURE:
<221> NAME/KEY: sig_peptide
<222> LOCATION: (-22)..(-1)
<220> FEATURE:
<221> NAME/KEY: mat_peptide
<222> LOCATION: (1)..(316)

<400> SEQUENCE: 4

Met Lys Phe Thr Val Ala Ile Thr Ser Ile Ala Val Ala Leu Ala Leu
            -20                 -15                 -10

Ser Ser Ser Ala Glu Ala Ala Ser Cys Ser Ser Val Tyr Gly Gln Cys
    -5                   1               5                   10

Gly Gly Ile Gly Trp Ser Gly Pro Thr Cys Cys Glu Ser Gly Ser Thr
                15                  20                  25

Cys Val Ala Gln Glu Gly Asn Lys Tyr Tyr Ser Gln Cys Leu Pro Gly
            30                  35                  40

Ser His Ser Asn Asn Ala Gly Asn Ala Ser Ser Thr Lys Lys Thr Ser
        45                  50                  55

Thr Lys Thr Ser Thr Thr Thr Ala Lys Ala Thr Ala Thr Val Thr Thr
    60                  65                  70

Lys Thr Val Thr Lys Thr Thr Lys Thr Thr Thr Lys Thr Ser Ser Thr
75                  80                  85                  90

Thr Ala Ala Ala Ser Thr Ser Thr Ser Ser Ser Ala Gly Tyr Lys Val
                95                  100                 105

Ile Ser Gly Gly Lys Ser Gly Ser Gly Ser Thr Thr Arg Tyr Trp Asp
            110                 115                 120

Cys Cys Lys Ala Ser Cys Ser Trp Pro Gly Lys Ala Ser Val Thr Gly
        125                 130                 135

Pro Val Asp Thr Cys Ala Ser Asn Gly Ile Ser Leu Leu Asp Ala Asn
    140                 145                 150

Ala Gln Ser Gly Cys Asn Gly Gly Asn Gly Phe Met Cys Asn Asn Asn
155                 160                 165                 170

Gln Pro Trp Ala Val Asn Asp Glu Leu Ala Tyr Gly Phe Ala Ala Ala
                175                 180                 185

Ser Ile Ala Gly Ser Asn Glu Ala Gly Trp Cys Cys Gly Cys Tyr Glu
            190                 195                 200

Leu Thr Phe Thr Ser Gly Ala Ala Ser Gly Lys Lys Met Val Val Gln
```

```
                205                 210                 215
Val Thr Asn Thr Gly Gly Asp Leu Gly Ser Asn His Phe Asp Leu Gln
    220                 225                 230

Met Pro Gly Gly Val Gly Ile Phe Asn Gly Cys Ala Ala Gln Trp
235                 240                 245                 250

Gly Ala Pro Asn Asp Gly Trp Gly Ala Arg Tyr Gly Gly Val Ser Ser
                255                 260                 265

Val Ser Asp Cys Ala Ser Leu Pro Ser Ala Leu Gln Ala Gly Cys Lys
                270                 275                 280

Trp Arg Phe Asn Trp Phe Lys Asn Ser Asp Asn Pro Thr Met Thr Phe
                285                 290                 295

Lys Glu Val Thr Cys Pro Ala Glu Leu Thr Thr Arg Ser Gly Cys Glu
    300                 305                 310

Arg Lys
315

<210> SEQ ID NO 5
<211> LENGTH: 387
<212> TYPE: PRT
<213> ORGANISM: Mucor circinelloides CP99001
<220> FEATURE:
<221> NAME/KEY: sig_peptide
<222> LOCATION: (-22)..(-1)
<220> FEATURE:
<221> NAME/KEY: mat_peptide
<222> LOCATION: (1)..(365)

<400> SEQUENCE: 5

Met Lys Phe Thr Val Ala Ile Thr Ser Ile Ala Val Ala Leu Ala Leu
        -20                 -15                 -10

Ser Ser Ser Ala Glu Ala Ala Ser Cys Ser Ser Val Tyr Gly Gln Cys
    -5                   1                   5                  10

Gly Gly Ile Gly Trp Thr Gly Pro Thr Cys Cys Asp Ala Gly Ser Thr
                15                  20                  25

Cys Lys Ala Gln Lys Asp Asn Lys Tyr Tyr Ser Gln Cys Ile Pro Lys
                30                  35                  40

Pro Lys Gly Ser Ser Ser Ser Ser Cys Ser Ser Val Tyr Ser Gln
            45                  50                  55

Cys Gly Gly Ile Gly Trp Ser Gly Pro Thr Cys Cys Glu Ser Gly Ser
            60                  65                  70

Thr Cys Val Ala Gln Glu Gly Asn Lys Tyr Tyr Ser Gln Cys Leu Pro
75                  80                  85                  90

Gly Ser His Ser Asn Asn Ala Gly Asn Ala Ser Ser Thr Lys Lys Thr
                95                  100                 105

Ser Thr Lys Thr Ser Thr Thr Ala Lys Ala Thr Ala Val Thr
            110                 115                 120

Thr Lys Thr Val Thr Lys Thr Thr Thr Lys Thr Thr Thr Lys Thr Ser
            125                 130                 135

Thr Thr Ala Ala Ala Ser Thr Ser Thr Ser Ser Ala Gly Tyr Lys
    140                 145                 150

Val Ile Ser Gly Gly Lys Ser Gly Ser Gly Ser Thr Thr Arg Tyr Trp
155                 160                 165                 170

Asp Cys Cys Lys Ala Ser Cys Ser Trp Pro Gly Lys Ala Ser Val Thr
                175                 180                 185

Gly Pro Val Asp Thr Cys Ala Ser Asn Gly Ile Ser Leu Leu Asp Ala
            190                 195                 200
```

-continued

```
Asn Ala Gln Ser Gly Cys Asn Gly Gly Asn Gly Phe Met Cys Asn Asn
        205                 210                 215

Asn Gln Pro Trp Ala Val Asn Asp Glu Leu Ala Tyr Gly Phe Ala Ala
        220                 225                 230

Ala Ser Ile Ala Gly Ser Asn Glu Ala Gly Trp Cys Cys Gly Cys Tyr
235                 240                 245                 250

Glu Leu Thr Phe Thr Ser Gly Ala Ala Ser Gly Lys Lys Met Val Val
                255                 260                 265

Gln Val Thr Asn Thr Gly Gly Asp Leu Gly Ser Asn His Phe Asp Leu
                270                 275                 280

Gln Met Pro Gly Gly Val Gly Ile Phe Asn Gly Cys Ala Ala Gln
        285                 290                 295

Trp Gly Ala Pro Asn Asp Gly Trp Gly Ala Arg Tyr Gly Gly Val Ser
        300                 305                 310

Ser Val Ser Asp Cys Ala Ser Leu Pro Ser Ala Leu Gln Ala Gly Cys
315                 320                 325                 330

Lys Trp Arg Phe Asn Trp Phe Lys Asn Ser Asp Asn Pro Thr Met Thr
                335                 340                 345

Phe Lys Glu Val Thr Cys Pro Ala Glu Leu Thr Thr Arg Ser Gly Cys
        350                 355                 360

Glu Arg Lys
        365

<210> SEQ ID NO 6
<211> LENGTH: 346
<212> TYPE: PRT
<213> ORGANISM: Phycomyces nitens CP99002
<220> FEATURE:
<221> NAME/KEY: sig_peptide
<222> LOCATION: (-19)..(-1)
<220> FEATURE:
<221> NAME/KEY: mat_peptide
<222> LOCATION: (1)..(327)

<400> SEQUENCE: 6

Met Lys Phe Ser Ile Ile Ala Ser Ala Leu Leu Ala Ala Ser Ser
            -15                 -10                  -5

Thr Tyr Ala Ala Glu Cys Ser Gln Gly Tyr Gly Gln Cys Gly Gly Lys
            1                   5                   10

Met Trp Thr Gly Pro Thr Cys Cys Thr Ser Gly Phe Thr Cys Val Gly
        15                  20                  25

Ala Glu Asn Asn Glu Trp Tyr Ser Gln Cys Ile Pro Asn Asp Gln Val
30                  35                  40                  45

Gln Gly Asn Pro Lys Thr Thr Thr Thr Thr Thr Lys Ala Ala Thr
            50                  55                  60

Thr Thr Lys Ala Pro Val Thr Thr Lys Ala Thr Thr Thr Thr
            65                  70                  75

Thr Lys Ala Pro Val Thr Thr Thr Lys Ala Thr Thr Thr Thr
            80                  85                  90

Lys Thr Thr Lys Thr Thr Thr Lys Ala Ala Thr Thr Thr Ser
            95                  100                 105

Ser Ser Asn Thr Gly Tyr Ser Pro Ile Ser Gly Phe Ser Gly Asn
110                 115                 120                 125

Gly Arg Thr Thr Arg Tyr Trp Asp Cys Cys Lys Pro Ser Cys Ala Trp
            130                 135                 140

Asp Gly Lys Ala Ser Val Thr Lys Pro Val Leu Thr Cys Ala Lys Asp
            145                 150                 155
```

```
Gly Val Ser Arg Leu Gly Ser Asp Val Gln Ser Gly Cys Val Gly Gly
        160                 165                 170

Gln Ala Tyr Met Cys Asn Asp Asn Gln Pro Trp Val Val Asn Asp Asp
        175                 180                 185

Leu Ala Tyr Gly Phe Ala Ala Ser Leu Gly Ser Ala Gly Ala Ser
190                 195                 200                 205

Ala Phe Cys Cys Gly Cys Tyr Glu Leu Thr Phe Thr Asn Thr Ala Val
                    210                 215                 220

Ala Gly Lys Lys Phe Val Val Gln Val Thr Asn Thr Gly Asp Asp Leu
        225                 230                 235

Ser Thr Asn His Phe Asp Leu Gln Met Pro Gly Gly Val Gly Tyr
        240                 245                 250

Phe Asn Gly Cys Gln Ser Gln Trp Asn Thr Asn Thr Asp Gly Trp Gly
        255                 260                 265

Ala Arg Tyr Gly Gly Ile Ser Ser Ile Ser Glu Cys Asp Lys Leu Pro
270                 275                 280                 285

Thr Gln Leu Gln Ala Gly Cys Lys Trp Arg Phe Gly Trp Phe Lys Asn
            290                 295                 300

Ala Asp Asn Pro Glu Val Thr Phe Lys Ala Val Thr Cys Pro Ala Glu
                305                 310                 315

Ile Ile Ala Lys Thr Gly Cys Glu Arg Lys
            320                 325

<210> SEQ ID NO 7
<211> LENGTH: 1257
<212> TYPE: DNA
<213> ORGANISM: Humicola insolens
<220> FEATURE:
<221> NAME/KEY: intron
<222> LOCATION: (453)..(509)

<400> SEQUENCE: 7
aatgacgggg caacctcccg cccgggccca actcttgggt ttggtttgac aggccgtctg      60
tctcttgcgt cctcttacta cgcctgcctg gaccctacgt ctcaactccg attcaagatg     120
cgttcctccc ctctcctccg ctccgccgtt gtggccgccc tgccggtgtt ggcccttgcc     180
gctgatggca gtccaccccg ctactgggac tgctgcaagc cttcgtgcgg ctgggccaag     240
aaggctcccg tgaaccagcc tgtcttctcc tgcaacgcca acttccagcg tctcactgac     300
ttcgacgcca gtccggctg cgagccgggc ggtgtcgcct actcgtgcgc cgaccagacc     360
ccatgggctg tgaacgacga cttcgcgttc ggttttgctg ccacctctat tgccggcagc     420
aatgaggcgg gctggtgctg cgcctgctac gagtaagctt tggtcgcgtg tgtaacactg     480
tgcaggcata gcactaacca cctcccaggc tcaccttcac atccggtcct gttgctggca     540
agaagatggt cgtccagtcc accagcactg gcggtgatct tggcagcaac cacttcgatc     600
tcaacatccc cggcggcggc gtcggcatct tcgacggatg cactccccag ttcggcggtc     660
tgccccggcca cgctacggc ggcatctcgt cccgcaacga gtcgatcgg ttcccccgacg     720
ccctcaagcc cggctgctac tggcgcttcg actggttcaa gaacgccgac aacccgagct     780
tcagcttccg tcaggtccaa tgcccagccg agctcgtcgc tcgcaccgga tgccgccgca     840
acgacgacgg caacttccct gccgtccaga tcccctccag cagcaccagc tctccggtcg     900
gccagcctac cagtaccagc accacctcca cctccaccac ctcgagcccg cccgtccagc     960
ctacgactcc cagcggctgc actgctgaga ggtgggctca gtgcggcggc aatggctgga    1020
```

```
gcggctgcac cacctgcgtc gctggcagca cctgcacgaa gattaatgac tggtaccatc   1080
agtgcctgta aacgcagggc agcctgagaa ccttactggt tgcgcaacga aatgacactc   1140
ccaatcactg tattagttct tgtacataat ttcgtcatcc ctccagggat tgtcacatat   1200
atgcaatgat gaatactgaa cacaaacctg gccgcttgaa ctggccgaag gaatgcc     1257
```

<210> SEQ ID NO 8
<211> LENGTH: 1720
<212> TYPE: DNA
<213> ORGANISM: Trichoderma viride
<220> FEATURE:
<221> NAME/KEY: intron
<222> LOCATION: (500)..(682)

<400> SEQUENCE: 8

```
ggtgtgtcat ttctcctcaa catactgcct ttcaacaact ttcgcctcct ccctggcctg    60
atatcccaat atcagttttt cccaaagtag caagtcatca gtaaatctgc tcatctatca   120
ttaatcagtg cccatagtgt ctgtctgttg attgcctccc gccatacacg atgaacagga   180
ccatggctcc attgctgctt gcagcgtcga tactcttcgg gggcgctgct gcacaacaga   240
ctgtctgggg acagtgtgga ggtattggtt ggagcggacc tacgagttgt gctcctggat   300
cagcttgttc tactctcaat ccttattatg cgcaatgcat tccggggggcc actagtatca   360 ccacctcgac ccgacccccc tcgggtccaa ccaccaccac cagagccacc tcaacgacct   420
catctccgcc accgaccagc tctggagttc gatttgctgg cgttaacatc gcgggctttg   480
acttcggatg taccacagag tatgtcttca tgttgcatag tgttgctggc tgagtattct   540
gggcggatga tttatagctg tgcgggctgc aaaacaccgc cggtctgcca ctatcaaggc   600
atagttgata ggcggcggtg ttttcttcaa tcccctgatt acactctcaa gaatctagtg   660
gctgatggat gtatgattac agtggcactt gcgttacatc gaaggtttat cctccgttga   720
agaacttcac tggggcaaac aactacccgg acggtatcgg ccagatgcag cacttcgtca   780
acgatgatgg gatgactatt ttccgcctac ccgtcggatg gcagtacctc gtaaacaaca   840
atctgggtga aactctcgat tccaccagta tctcgaagta tgatcagctc gttcagggt   900 gcctgtctct cggtgtatac tgcatcatcg acatccacaa ttatgctcga tggaacggtg   960
gaatcattgg ccagggaggc cctacaaatg cccagtttac cagtctttgg tcgcagttgg  1020
catcgaagta cgcgtctcag tcgagggtgt ggttcggaat aatgaatgag ccccacgacg  1080
tgaacatcaa cacttgggct gccacggttc aagaggtcgt cactgcaatc cgcaacgccg  1140
gtgctacgtc gcaatacatt tctctgcctg gaaatgatta tcaatctgcg gcagctttta  1200
tttccgatgg cagtgcagcc gccctgtctc aggtaacgaa ccctgatgga tcaacaacga  1260
atctaatctt cgatgtccac aagtacttag actcggacaa ctccggtact cacgccgaat  1320
gcactacaaa caacatcgac ggcgcctttg ctcctctcgc cacttggctt cgacagaaca  1380
accgccaggc tattctgacg gaaaccggcg gtggcaatgt tcagtcctgc atccaagatt  1440
tgtgccaaca gatccagtac ctcaaccaga actcagatgt ctatcttggc tatgctggct  1500
ggggtgccgg ttcatttgat agcacttata ttctgacgga aacgcctact ggaagcggta  1560
actcgtggac ggacacatcc ctagttagct cgtgtctcgc caggaagtaa caccgaggtc  1620
gattgcagga gccttgtcaa tagcgatttc atcttgctgt acataattct tactctctga  1680
agccgcttgt tctgggtatg tgtcttgaca ggtttctaga                        1720
```

<210> SEQ ID NO 9

<211> LENGTH: 1043
<212> TYPE: DNA
<213> ORGANISM: Artificial Sequence
<220> FEATURE:
<223> OTHER INFORMATION: Description of Artificial Sequence:
      Codon-optimized sequence corresponding to RCEI
      protein (SEQ ID NO: 1)
<220> FEATURE:
<221> NAME/KEY: CDS
<222> LOCATION: (16)..(1032)
<220> FEATURE:
<221> NAME/KEY: sig_peptide
<222> LOCATION: (16)..(84)
<220> FEATURE:
<221> NAME/KEY: mat_peptide
<222> LOCATION: (85)..(1029)

<400> SEQUENCE: 9

```
ggatcctggg acaag atg aag ttc atc act atc gcc tcc tcc gcc ctc ctt        51
                Met Lys Phe Ile Thr Ile Ala Ser Ser Ala Leu Leu
                    -20              -15 gcc ctc gcc ctt ggc act gag atg gcc tcc gcc gct gag tgc tcc aag         99
Ala Leu Ala Leu Gly Thr Glu Met Ala Ser Ala Ala Glu Cys Ser Lys
    -10              -5                1                5 ctc tac gga cag tgc ggc gga aag aac tgg aac ggc ccc acc tgc tgc        147
Leu Tyr Gly Gln Cys Gly Gly Lys Asn Trp Asn Gly Pro Thr Cys Cys
             10              15                  20 gag agc ggc tcg acc tgc aag gtc tcg aat gac tac tac agc cag tgc        195
Glu Ser Gly Ser Thr Cys Lys Val Ser Asn Asp Tyr Tyr Ser Gln Cys
            25                  30                  35 ctg ccg agc ggc tcc tcg gga aac aag tcg agc gag tcg gcc cac aag        243
Leu Pro Ser Gly Ser Ser Gly Asn Lys Ser Ser Glu Ser Ala His Lys
        40                  45                  50 aag acc acg acc gct gcc cac aag aag acc acg acc gcc gct cac aag        291
Lys Thr Thr Thr Ala Ala His Lys Lys Thr Thr Thr Ala Ala His Lys
    55                  60                  65 aag act acg acc gct ccc gcc aag aag acc acg acc gtc gcc aag gct        339
Lys Thr Thr Thr Ala Pro Ala Lys Lys Thr Thr Thr Val Ala Lys Ala
70                  75                  80                  85 tcg act ccg tcc aac tcg agc agc tcg tct tcg gga aag tac agc gct        387
Ser Thr Pro Ser Asn Ser Ser Ser Ser Ser Gly Lys Tyr Ser Ala
                90                  95                  100 gtc agc ggt ggc gct agc ggc aac ggc gtc act acc cgc tac tgg gac        435
Val Ser Gly Gly Ala Ser Gly Asn Gly Val Thr Thr Arg Tyr Trp Asp
            105                 110                 115 tgc tgc aag gct tcg tgc tcg tgg ccc ggc aag gct aac gtc agc tcg        483
Cys Cys Lys Ala Ser Cys Ser Trp Pro Gly Lys Ala Asn Val Ser Ser
        120                 125                 130 cct gtc aag tcc tgc aac aag gac ggc gtc acc gct ctt agc gac tcc        531
Pro Val Lys Ser Cys Asn Lys Asp Gly Val Thr Ala Leu Ser Asp Ser
    135                 140                 145 aac gcc cag tcc ggc tgc aac ggc ggc aac tcc tac atg tgc aac gac        579
Asn Ala Gln Ser Gly Cys Asn Gly Gly Asn Ser Tyr Met Cys Asn Asp
150                 155                 160                 165 aac cag cca tgg gct gtc aac gac aac ctt gct tac ggt ttc gct gcc        627
Asn Gln Pro Trp Ala Val Asn Asp Asn Leu Ala Tyr Gly Phe Ala Ala
                170                 175                 180 gct gcc att agc ggc ggt ggc gag agc cgc tgg tgc tgc tcc tgc ttc        675
Ala Ala Ile Ser Gly Gly Gly Glu Ser Arg Trp Cys Cys Ser Cys Phe
            185                 190                 195 gag ctc acc ttc acc tcc acc agc gtt gct ggc aag aag atg gtc gtc        723
Glu Leu Thr Phe Thr Ser Thr Ser Val Ala Gly Lys Lys Met Val Val
        200                 205                 210
```

-continued

```
cag gtc acc aac act ggc ggt gac ctt ggc agc tcg acc ggt gcc cac      771
Gln Val Thr Asn Thr Gly Gly Asp Leu Gly Ser Ser Thr Gly Ala His
    215                 220                 225 ttc gat ctc cag atg ccc ggc ggc ggc gtc ggc atc ttc aac gga tgc      819
Phe Asp Leu Gln Met Pro Gly Gly Gly Val Gly Ile Phe Asn Gly Cys
230                 235                 240                 245 tcg tcc cag tgg ggc gct ccc aac gac ggc tgg ggc tcg cgc tac ggc      867
Ser Ser Gln Trp Gly Ala Pro Asn Asp Gly Trp Gly Ser Arg Tyr Gly
                250                 255                 260 ggc atc agc tcc gcc agc gac tgc tcg tcc ctc ccc agc gcc ctc cag      915
Gly Ile Ser Ser Ala Ser Asp Cys Ser Ser Leu Pro Ser Ala Leu Gln
            265                 270                 275 gcc ggc tgc aag tgg cgc ttc aac tgg ttc aag aac gcc gac aac ccg      963
Ala Gly Cys Lys Trp Arg Phe Asn Trp Phe Lys Asn Ala Asp Asn Pro
        280                 285                 290 tcc atg acc tac aag gag gtc acc tgc ccc aag gag atc acc gct aag     1011
Ser Met Thr Tyr Lys Glu Val Thr Cys Pro Lys Glu Ile Thr Ala Lys
    295                 300                 305 acc gga tgc tcg cgc aag taa acgcaggatc c                            1043
Thr Gly Cys Ser Arg Lys
310                 315
```